United States Patent [19]

Chen

[11] Patent Number: 5,737,926
[45] Date of Patent: Apr. 14, 1998

[54] CRYOGENIC STERILE NITROGEN SYSTEM

[75] Inventor: Alan Tat Yan Chen, Livingston, N.J.

[73] Assignee: Praxair Technology, Inc., Danbury, Conn.

[21] Appl. No.: 837,409

[22] Filed: Apr. 17, 1997

[51] Int. Cl.$^6$ .................................................. F17C 9/02
[52] U.S. Cl. .............................. 62/50.2; 62/908; 422/28
[58] Field of Search .................. 62/50.2, 908; 422/28

[56] References Cited

U.S. PATENT DOCUMENTS

| | | | |
|---|---|---|---|
| 3,500,652 | 3/1970 | Manns et al. | 62/908 |
| 4,620,962 | 11/1986 | Brodbeck | 422/24 |
| 4,759,848 | 7/1988 | Segura et al. | 210/651 |
| 5,182,926 | 2/1993 | Carns et al. | 62/908 |
| 5,533,345 | 7/1996 | Schvester et al. | 62/50.1 |
| 5,548,962 | 8/1996 | Luger et al. | 62/908 |

*Primary Examiner*—Ronald C. Capossela
*Attorney, Agent, or Firm*—Stanley Ktorides

[57] ABSTRACT

A system for producing cryogenic sterile nitrogen wherein liquid nitrogen is first vaporized and subsequently heated prior to undergoing sterilization, the warm sterilized nitrogen vapor is cooled to effect the vaporization of the liquid nitrogen, and the resulting cooled sterilized nitrogen is condensed to produce the product cryogenic sterile nitrogen. The system may be used to produce other cryogenic sterile cryogens also.

10 Claims, 1 Drawing Sheet

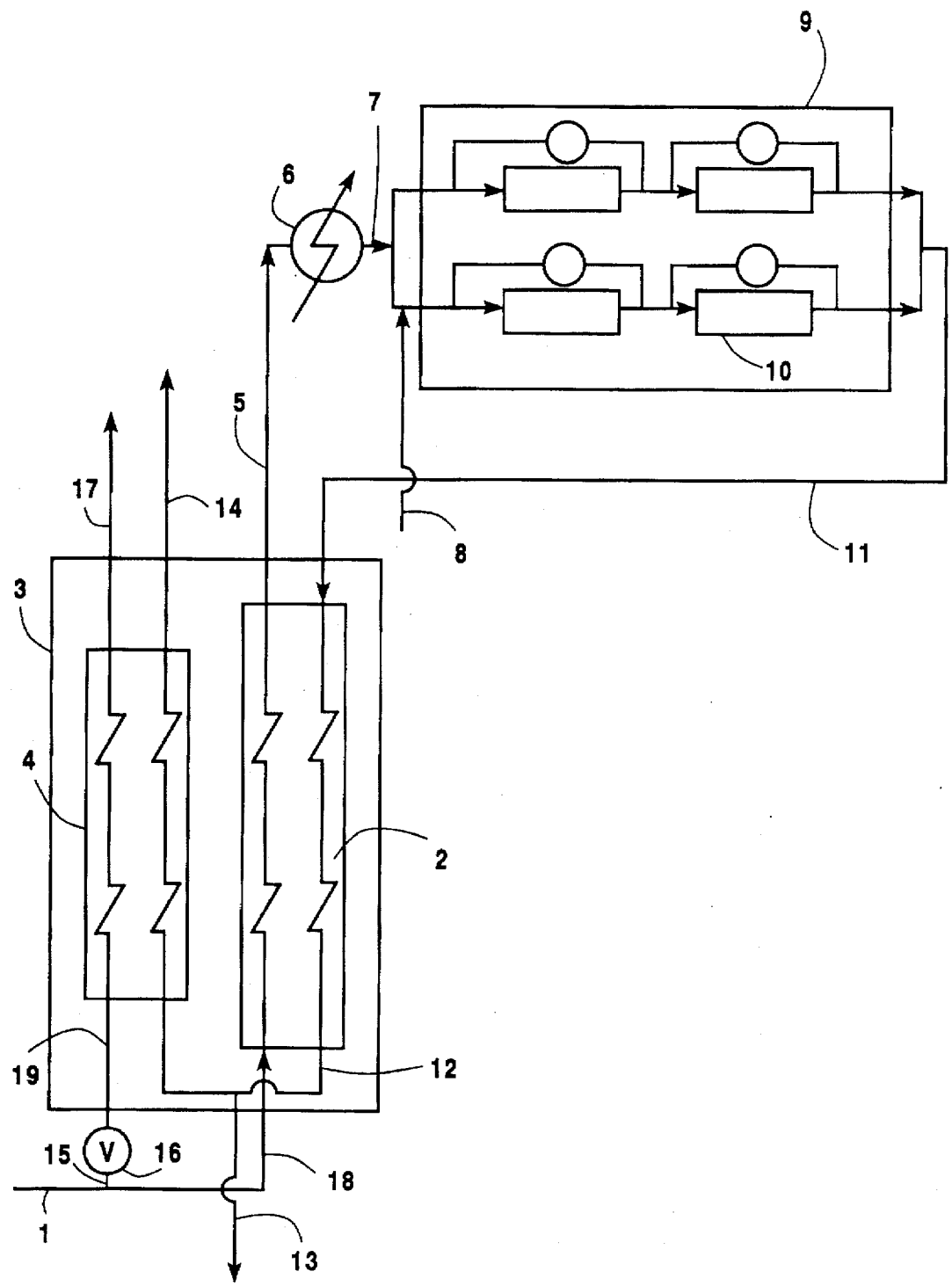

CRYOGENIC STERILE NITROGEN SYSTEM

TECHNICAL FIELD

This invention relates to the production of sterile cryogen such as sterile nitrogen. Other sterile cryogens which could be produced with the practice of this invention including sterile argon, carbon dioxide, oxygen, helium, and hydrogen.

BACKGROUND ART

Liquid nitrogen is widely used to cool or freeze articles. While this cooling or freezing may be carried out by indirect heat exchange, direct heat exchange involving direct contact of the nitrogen with the articles is preferred because there is a more efficient transfer of refrigeration from the nitrogen to the articles. However, in some situations such as in the preparation of pharmaceuticals such as antibiotics or vaccines, the use of liquid nitrogen as a direct contact coolant must be foregone unless the liquid nitrogen is sterile because, although bacteria and other microorganisms are inactive at the cryogenic temperatures of liquid nitrogen, such bacteria and other microorganisms can become active once the cooled or frozen article is at a higher temperature.

Accordingly it is an object of this invention to provide a system for effectively and efficiently producing cryogenic sterile nitrogen as well as other sterile cryogens.

SUMMARY OF THE INVENTION

The above and other objects, which will become apparent to those skilled in the art upon a reading of this disclosure, are attained by the present invention, one aspect of which is:

A method for producing cryogenic sterile nitrogen comprising:

(A) vaporizing liquid nitrogen to produce cold nitrogen vapor;

(B) warming the cold nitrogen vapor to produce warm nitrogen vapor;

(C) sterilizing the warm nitrogen vapor to produce sterile warm nitrogen vapor;

(D) cooling the sterile warm nitrogen vapor by indirect heat exchange with said vaporizing liquid nitrogen to produce cool sterile nitrogen vapor and said cold nitrogen vapor; and (E) condensing the cool sterile nitrogen vapor to produce product cryogenic sterile nitrogen.

Another aspect of the invention:

Apparatus for producing cryogenic sterile cryogen comprising:

(A) an evaporator and means for passing liquid cryogen into the evaporator;

(B) a heater and means for passing fluid from the evaporator to the heater;

(C) a biological filter and means for passing fluid from the heater to the biological filter;

(D) a condenser, means for passing fluid from the biological filter to the evaporator, and means for passing fluid from the evaporator to the condenser; and (E) means for recovering product cryogenic sterile cryogen from the condenser.

As used herein, the term "indirect heat exchange" means the bringing of two fluid streams into heat exchange relation without any physical contact or intermixing of the fluids with each other.

As used herein, the term "cryogenic" means having a temperature at or less than −70° C.

As used herein the term "sterile" means containing no biological agents larger than 0.2 microns in diameter.

As used herein, the term "biological filter" means a filter having pores which are not larger than 0.2 microns in diameter.

BRIEF DESCRIPTION OF THE DRAWING

The sole FIGURE is a schematic representation of one preferred embodiment of the invention for producing cryogenic sterile cryogen.

DETAILED DESCRIPTION

The most important sterile cryogen from a commercial standpoint is sterile nitrogen. Accordingly, the invention will be described in detail with reference to the FIGURE and in conjunction with the production of sterile nitrogen. Referring now to the FIGURE, liquid nitrogen 1 is passed from a source (not shown) of liquid nitrogen such as a storage tank, through conduit means into first heat exchanger or evaporator 2 which is located within cold box 3. Liquid nitrogen 1 has a nitrogen concentration of at least 60 mole percent, preferably at least 95 mole percent, and is at a pressure generally within the range of from 16 to 250 pounds per square inch absolute (psia) and at a temperature of about −160° C. or less at 250 psig. Cold box 3 is an insulated container which preferably also houses second heat exchanger or condenser 4.

Within evaporator 2 the liquid nitrogen is vaporized to produce cold nitrogen vapor 5 having a temperature generally within the range of from about −160° to −195° C. at 250 psig. Cold nitrogen vapor 5 is passed to heater 6 wherein it is warmed to a temperature of at least −50° C. and generally within the range of from −20° C. to 30° C. to produce warm nitrogen vapor 7. Preferably the warm nitrogen vapor is at ambient temperature. The temperature of the warm nitrogen vapor should exceed the embrittlement temperature and glass transition temperature of the filter module materials.

Warm nitrogen vapor 7 is passed to a biological filter wherein it is sterilized to produce sterile warm nitrogen vapor. In the embodiment of the invention illustrated in the FIGURE, steam 8 is used for sterilization purposes and the nitrogen fluid is passed to module 9 containing four biological filters 10 and emerges as sterile warm nitrogen vapor 11.

Prior to the start of the sterile nitrogen production, steam 8 is provided to the biological filters and is passed through the biological filters for several hours to sterilize module 9 and all the attendant passageways by heating to at least 110° C. The steam is then turned off and gas, such as nitrogen gas, is passed through the system for 24 to 48 hours to dry the system. When the system is totally dried, the warm nitrogen vapor is produced as has been described and is passed through the biological filter or filters and emerges therefrom as sterile nitrogen vapor.

Sterile warm nitrogen vapor 11 is passed by conduit from the biological filters of biological filter module 9 to evaporator 2 wherein the heat within the sterile warm nitrogen vapor is used to vaporize by indirect heat exchange the vaporizing liquid nitrogen as was previously described to produce cold nitrogen vapor 5. In the course of this heat exchange the sterile warm nitrogen vapor is cooled to produce cool sterile nitrogen vapor having a temperature generally within the range of from −157° to −193° C.

Cool sterile nitrogen vapor 12 is passed from evaporator 2 to condenser 4. If desired, as illustrated in the FIGURE, a drain line 13 may be connected to the conduit in which cool sterile nitrogen vapor is passed from evaporator 2 to condenser 4 for removal of steam condensate. Within condenser 4 the cool sterile nitrogen vapor is condensed by indirect heat exchange to produce cryogenic sterile nitrogen 14 which is recovered as product. The product cryogenic sterile nitrogen may be used directly, in whole or in part, for cooling and/or freezing purposes, or may be passed, in whole or in part, to storage prior to use. The embodiment illustrated in the FIGURE is a preferred embodiment wherein a portion 15 of liquid nitrogen 1 is reduced in pressure by passage through valve 16 and is passed into condenser 4 as stream 19 wherein it is vaporized to effect the aforesaid condensation of the cool sterile nitrogen vapor. Resulting gaseous nitrogen 17 is then withdrawn from condenser 4. When stream 15 is used, the portion of stream 1 passed to evaporator 2 as the liquid nitrogen is designated as stream 18.

The following is a tabular summary of an example of the invention wherein sterile liquid nitrogen is produced at the rate of 850 lb./hr. (11,902 cf/hr. at NTP). The example is of an embodiment of the invention similar to that illustrated in the FIGURE and the stream numbers in the tabular summary correspond to those of the FIGURE. The example is presented for illustrative purposes and is not intended to be limiting.

|  | INLET | OUTLET | CHANGE | FLOW CFH @ NTP | EST. ENERGY (KW) |
|---|---|---|---|---|---|
| STREAM | 18 | 5 |  | 11,902 | 23.9 |
| TEMP (C.) | −176.5 | −137 | 39.5 |  |  |
| PRESS (PSIG) | 75 | 70 |  |  |  |
| FORM | LN2 | GN2 |  |  |  |
| STREAM | 5 | 7 |  | 11,902 | 19.9 |
| TEMP (C.) | −137 | 26.8 | 163.8 |  |  |
| PRESS (PSIG) | 70 | 70 | 0 |  |  |
| FORM | GN2 | GN2 |  |  |  |
| STREAM | 7 | 11 |  | 11,902 |  |
| TEMP (C.) | 26.8 | 26.8 | 0 |  |  |
| PRESS (PSIG) | 70 | 60 | −10 |  |  |
| FORM | GN2 | GN2 |  |  |  |
| STREAM | 11 | 12 |  | 11,902 | −23.9 |
| TEMP (C.) | 26.8 | −173.5 | −200.3 |  |  |
| PRESS (PSIG) | 60 | 55 | −5 |  |  |
| FORM | GN2 | GN2 |  |  |  |
| STREAM | 12 | 14 |  | 11,902 | 20.4 |
| TEMP (C.) | −173.5 | −180.7 | −7.2 |  |  |
| PRESS (PSIG) | 55 | 50 | −5 |  |  |
| FORM | GN2 | LN2 |  |  |  |
| STREAM | 19 | 17 |  | 12,131 | 20.4 |
| TEMP (C.) | −184.3 | −185.5 | 1.2 |  |  |
| PRESS (PSIG) | 33 | 28 | −5 |  |  |
| FORM | LN2 | GN2 |  |  |  |

Now by the use of this invention one can effectively produce cryogenic sterile nitrogen. Although the invention has been described in detail with reference to a certain preferred embodiment, those skilled in the art will recognize that there are other embodiments of the invention within the spirit and the scope of the claims. For example, as discussed above, other sterile cryogens may be produced with the practice of this invention. It is recognized that the sterile cryogen produced, e.g. sterile nitrogen, may be pure, e.g. 100 percent nitrogen, or may be a mixture containing less than 100 percent of the cryogen species. A rigorous definition of the general method of the invention is as follows:

A method for producing cryogenic sterile cryogen comprising:

(A) vaporizing liquid cryogen to produce cold vapor;

(B) warming the cold vapor to produce warm vapor;

(C) sterilizing the warm vapor to produce sterile warm vapor;

(D) cooling the sterile warm vapor by indirect heat exchange with said vaporizing liquid cryogen to produce cool sterile vapor and said cold vapor; and (E) condensing the cool sterile vapor to produce product cryogenic sterile cryogen.

I claim:

1. A method for producing cryogenic sterile nitrogen comprising:

(A) vaporizing liquid nitrogen to produce cold nitrogen vapor;

(B) warming the cold nitrogen vapor to produce warm nitrogen vapor;

(C) sterilizing the warm nitrogen vapor to produce sterile warm nitrogen vapor;

(D) cooling the sterile warm nitrogen vapor by indirect heat exchange with said vaporizing liquid nitrogen to produce cool sterile nitrogen vapor and said cold nitrogen vapor; and (E) condensing the cool sterile nitrogen vapor to produce product cryogenic sterile nitrogen.

2. The method of claim 1 further comprising adding steam to the warm nitrogen vapor to carry out the sterilization of the warm nitrogen vapor to produce sterile warm nitrogen vapor.

3. The method of claim 1 wherein the cool sterile nitrogen vapor is condensed by indirect heat exchange with liquid nitrogen which is at a pressure less than that of the cool sterile nitrogen vapor.

4. The method of claim 1 wherein the warm nitrogen vapor is sterilized by passage through a biological filter.

5. Apparatus for producing cryogenic sterile cryogen comprising:

(A) an evaporator and means for passing liquid cryogen into the evaporator;

(B) a heater and means for passing fluid from the evaporator to the heater;

(C) a biological filter and means for passing fluid from the heater to the biological filter;

(D) a condenser, means for passing fluid from the biological filter to the evaporator, and means for passing fluid from the evaporator to the condenser; and (E) means for recovering product cryogenic sterile cryogen from the condenser.

6. The apparatus of claim 5 further comprising means for providing steam to the biological filter.

7. The apparatus of claim 5 further comprising means for providing liquid cryogen into the condenser and means for withdrawing gaseous fluid from the condenser.

8. A method for producing cryogenic sterile cryogen comprising:

(A) vaporizing liquid cryogen to produce cold vapor;

(B) warming the cold vapor to produce warm vapor;

(C) sterilizing the warm vapor to produce sterile warm vapor;

(D) cooling the sterile warm vapor by indirect heat exchange with said vaporizing liquid cryogen to produce cool sterile vapor and said cold vapor; and (E) condensing the cool sterile vapor to produce product cryogenic sterile cryogen.

9. The method of claim 8 wherein the cryogen comprises argon.

10. The method of claim 8 wherein the cryogen comprises carbon dioxide.

* * * * *

UNITED STATES PATENT AND TRADEMARK OFFICE
CERTIFICATE OF CORRECTION

PATENT NO. : 5,737,926
DATED : April 14, 1998
INVENTOR(S) : A. T. Y. Cheng

It is certified that error appears in the above-identified patent and that said Letters Patent is hereby corrected as shown below:

On title page, item [19]
In the inventor's name delete "Chen" and insert therefor --Cheng--.

Signed and Sealed this

Sixteenth Day of June, 1998

Attest:

BRUCE LEHMAN

Attesting Officer     Commissioner of Patents and Trademarks